United States Patent
Rogers et al.

(10) Patent No.: US 12,428,382 B2
(45) Date of Patent: Sep. 30, 2025

(54) PURIFICATION OF SUBSTITUTED DIAMINOPYRAZINE DICARBOXYLIC ACIDS

(71) Applicant: MediBeacon Inc., St. Louis, MO (US)

(72) Inventors: Thomas Rogers, St. Louis, MO (US); David Adams, St. Louis, MO (US); Xiaogang Hua, St. Louis, MO (US)

(73) Assignee: MEDIBEACON INC., St. Louis, MO (US)

( * ) Notice: Subject to any disclaimer, the term of this patent is extended or adjusted under 35 U.S.C. 154(b) by 652 days.

(21) Appl. No.: 17/697,281

(22) Filed: Mar. 17, 2022

(65) Prior Publication Data

US 2022/0315538 A1 Oct. 6, 2022

Related U.S. Application Data

(60) Provisional application No. 63/168,518, filed on Mar. 31, 2021.

(51) Int. Cl.
 *C07D 241/32* (2006.01)
 *C07D 241/28* (2006.01)

(52) U.S. Cl.
 CPC ......... *C07D 241/32* (2013.01); *C07D 241/28* (2013.01)

(58) Field of Classification Search
 CPC .. C07D 241/02; C07D 241/32; C07D 241/20; C07D 241/34; A61K 31/4965
 USPC ..................... 544/407; 514/255.06
 See application file for complete search history.

(56) References Cited

U.S. PATENT DOCUMENTS

| | | |
|---|---|---|
| 2013/0136698 A1 | 5/2013 | Neumann et al. |
| 2019/0125901 A1 | 5/2019 | Debreczeny et al. |
| 2019/0154697 A1* | 5/2019 | Shieh ...................... G01N 1/28 |

FOREIGN PATENT DOCUMENTS

| | | |
|---|---|---|
| WO | 2010/078025 A1 | 7/2010 |
| WO | 2016/183351 A1 | 11/2016 |

OTHER PUBLICATIONS

PubChem, "Serine", first created 2004, National Library of Medicine, 89 pgs. (Year: 2004).*
International Search Report and Written Opinion for PCT/US2022/020754 dated Jun. 14, 2022, 9 pages.
International Search Report and Written Opinion for PCT/US2022/020789 dated Jun. 14, 2022, 8 pages.
Subiros-Funosas, et al. "Oxyma: An Efficient Additive for Peptide Synthesis to Replace the Benzotriazole-Based HOBt and HOAt with a Lower Risk of Explosion", Chem. Eur. J., 2009, 15:9394-9403.
PubChem-CID-71077, "D-serine", created Sep. 16, 2004, retrieved at https://pubchem.ncbi.nlm.nih.gov/compound/71077.
PubChem-CID-9085, "L-Homoarginine", created Jun. 24, 2005, retrieved at https://pubchem.ncbi.nlm.nih.gov/compound/9085.
Rajagopalan, R. et al., "Hydrophilic Pyrazine Dyes as Exogenous Fluorescent Tracer Agents for Real-Time Point-of-Care Measurement of Glomerular Filtration Rate" Journal of Medicinal Chemistry, 2011, 54:5048-5058.
Extended European Search Report issued Oct. 3, 2025 from related EP Application No. 22781870.5, 7 pgs.
Extended European Search Report issued Mar. 13, 2025 from related EP Application 22781873.9, 8 pgs.

* cited by examiner

Primary Examiner — Jeffrey H Murray
Assistant Examiner — Madeline E Braun
(74) *Attorney, Agent, or Firm* — POLSINELLI PC

(57) ABSTRACT

The present invention provides methods for the purification of the compound of Formula (I) from the precipitated reaction product comprising the compound of Formula (I), impurities, and/or residual or entrained solvents.

30 Claims, 3 Drawing Sheets

PURIFICATION OF SUBSTITUTED DIAMINOPYRAZINE DICARBOXYLIC ACIDS

CROSS-REFERENCE TO RELATED APPLICATIONS

This application claims priority to U.S. Provisional Application No. 63/168,518 filed Mar. 31, 2021, the contents of which are incorporated herein by reference in their entirety.

FIELD OF THE INVENTION

The present disclosure generally relates to methods of purification of the compound of Formula (I) from the precipitated reaction product comprising the compound of Formula (I), impurities, and/or residual or entrained solvents.

BACKGROUND OF THE INVENTION 3,6-Diamino-2,5-bis{N-[(1R)-1-carboxy-2-hydroxyethyl]-carbamoyl}pyrazine] (referred to MB-102) is a non-radioactive, exogenous agents useful for the monitoring of renal function in a human subject. The preparation of 3,6-diamino-2,5-bis{N-[(1R)-1-carboxy-2-hydroxyethyl]-carbamoyl}pyrazine] is prepared through a four-step method as disclosed in the literature as shown in FIG. 1. Step 1 of this four-step process hydrolyzes the aromatic nitrile groups of compound 1 using concentrated sulfuric acid forming the dicarboxamide compound 2. Step 2 hydrolyzes the dicarboxamide groups on compound 2 yielding dicarboxylic acid compound 3 (referred to as MB-301). Step 3 entails the coupling of compound 3 using HOBt (hydroxybenzotriazole), EDC HCl, diisopropylethylamine in N,N-dimethylformamide with the benzyl ester of (R) serine HCl yielding the product, compound 4 (referred to MP-3269). In order to remove impurities and provide a high purity of compound 4, the crude compound 4 is generally purified by chromatography. The purified compound 4 undergoes reductive debenzylation to form 3,6-diamino-2,5-bis{N-[(1R)-1-carboxy-2-hydroxyethyl]-carbamoyl}pyrazine] compound 5 in Step 4.

A main problem in further developing this process to a GMP (Good Manufacturing Practice) process is identified in Step 3 of the process. Step 3 utilizes chromatography and requires large quantities of various solvents to remove impurities and increase the purity of compound 4. The chromatography and the amounts of solvents increase the overall cost of the compound 4 and increases the waste for the process.

In early process development, Step 3 of the above process was examined. Step 3 was initially examined to reduce the amount of DMF in the process. This reduction in DMF would improve waste factor and reduce the cost of the process. From these initial process development experiments, the minimum amount of DMF was found necessary to provide solubility and allow Step 3 to proceed to completion. Then, DMF from the reaction mixture needed to be removed. Generally, a large excess of DMF can be removed using a large excess of water (~50-100× of water to the amount of DMF) and compound 4 would precipitate. With using large amounts of water in the precipitation, the overall waste factor of the process would increase. An alternate method to remove DMF was investigated. Experiments were conducted to remove the DMF from the completed method step through distillation before precipitation. This distillation provided a new impurity, namely the N-formyl impurity compound 12. Attempts to use the crude compound 4 with small amounts of the N-formyl impurity 12 in Step 4 of the process yielded material containing small amounts of the N-formyl adduct which carried through from Step 3.

A new method for preparing compound 4 utilizes Oxyma and EDC HCl as the coupling reagents is disclosed in a co-pending application (U.S. Provisional Application No. 63/168,512 filed Mar. 31, 2021, the entire contents of which are incorporated by reference herein). This method is shown in FIG. 2 and the impurities from the crude process are shown in FIG. 3. Other impurities were found to be easily removed through crystallization of compound 4 from Step 3.

What is needed is an improved method to work-up and crystallize the impure MB-102 to form highly purified MB-102. This new method would eliminate the need for chromatography and reduce the impurities such as the N-formyl impurity compound 12.

FIGURES

SUMMARY OF THE INVENTION

Figure 1:
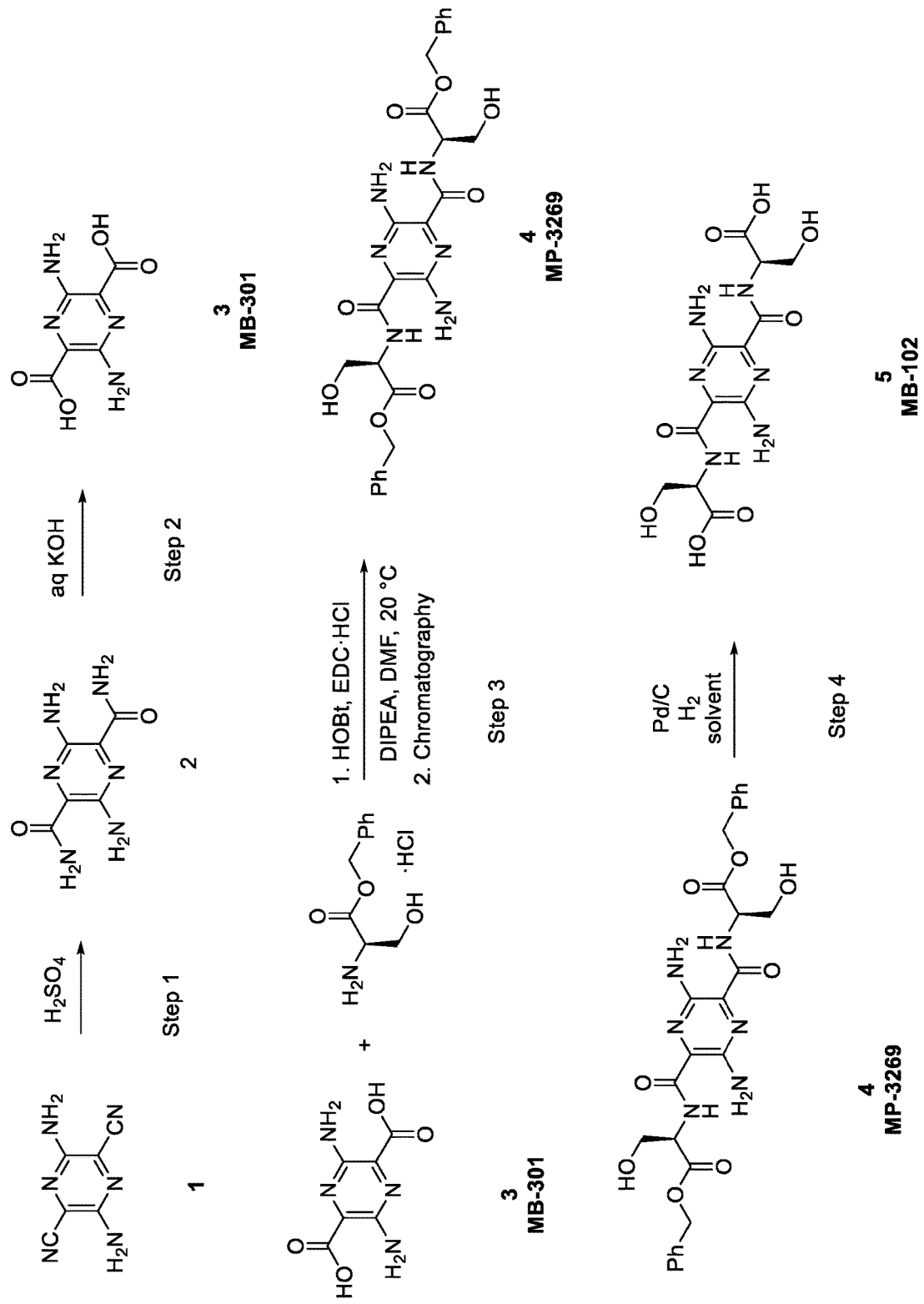
FIG. 1 illustrates the reaction scheme to prepare 3,6-diamino-2,5-bis{N-[(1R)-1-carboxy-2-hydroxyethyl]-carbamoyl}pyrazine] as depicted in literature methods.
Figure 2:
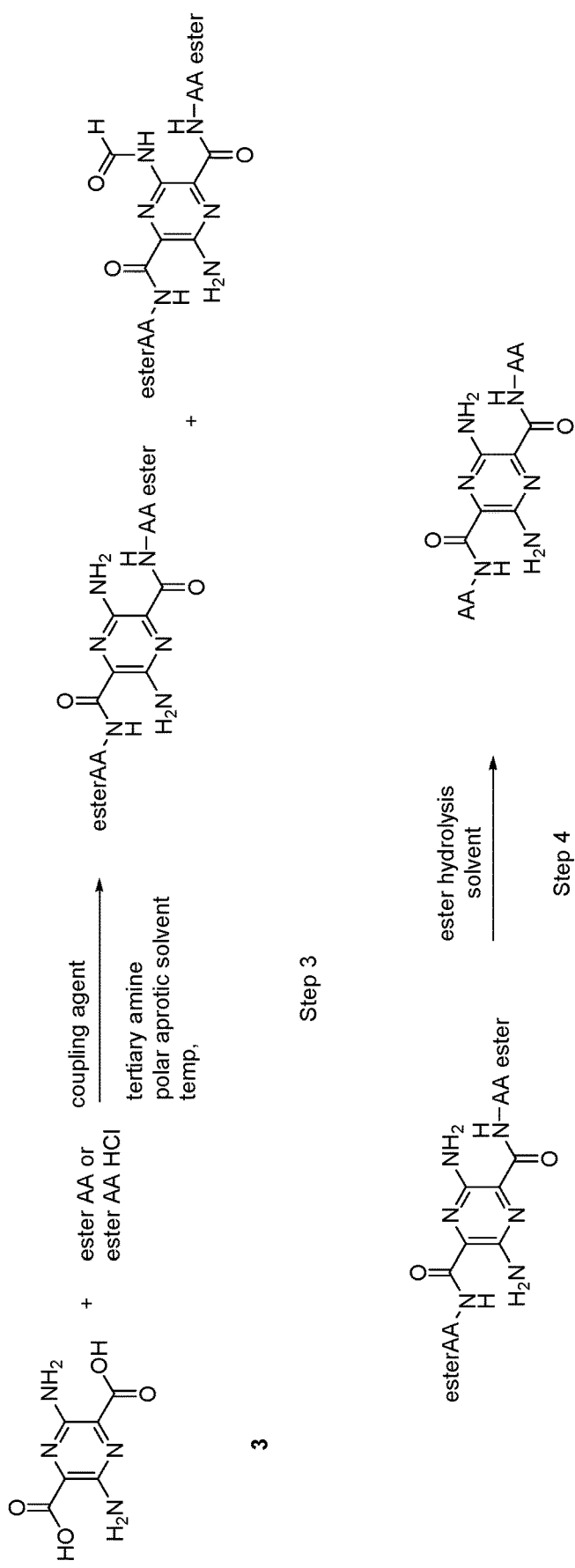
FIG. 2 illustrates reactions and optimization of Step 3 of the process.
Figure 3:
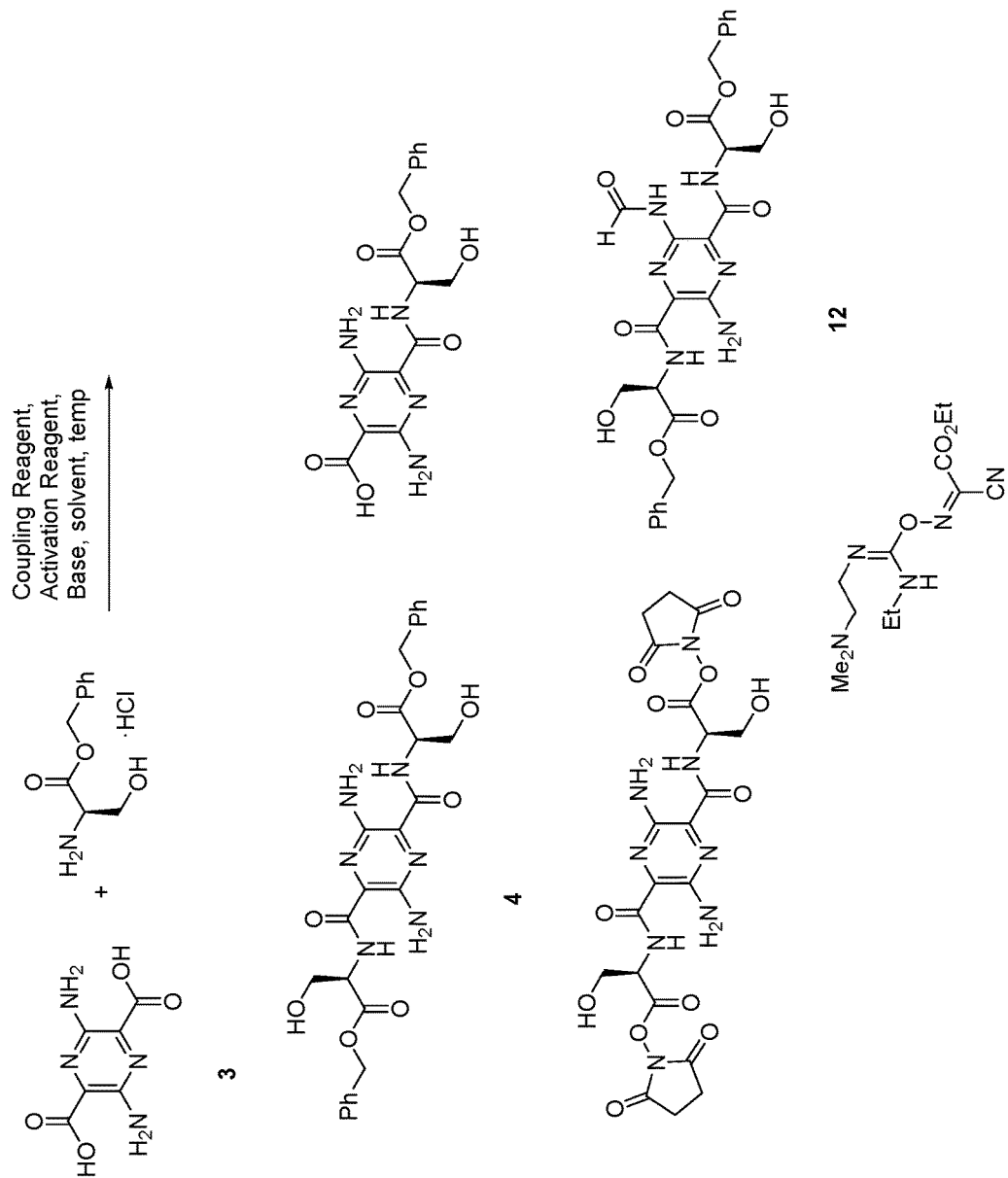
FIG. 3 illustrates the impurities derived during process development.

In one aspect, provided herein are method for purifying a compound of Formula (I) or salt thereof from the precipitated reaction product comprising the compound of Formula (I), impurities, and/or residual or entrained solvents,

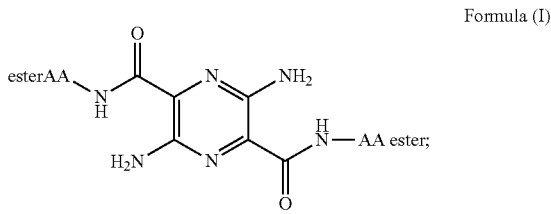

Formula (I)

the method comprising: (a) contacting the precipitated reaction product comprising the compound of Formula (I), impurities, and/or residual or entrained solvents with a solvent forming a first reaction mixture; (b) performing at least one distillation of the first reaction mixture under vacuum maintaining a temperature below 40° C. forming a second reaction mixture; and (c) cooling the second reaction mixture to a temperature of about 0° C.; and (d) isolating the compound of Formula (I) from the second reaction mixture; wherein the ester portion of the ester amino acid (AA ester) is an $C_1$-$C_{10}$ unsubstituted alkyl or a $C_1$-$C_{10}$ substituted alkyl.

Other features and iterations of the invention are described in more detail below.

DETAILED DESCRIPTION OF THE INVENTION

Before the present invention is disclosed and described, it is to be understood that this invention is not limited to the particular methods, compositions, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

Provided herein are methods for the purification of the compound of Formula (I) from the precipitated reaction product comprising the compound of Formula (I), impurities, and/or residual or entrained solvents. Advantageously, the compound of Formula (I), after purification, has a lower amounts of impurities, low residual solvents, low residual water, and can be readily utilized in the subsequent process steps.

(I) Method of Purification of the Compound of Formula (I)

In one aspect, the present disclosure encompasses methods for the purification of the compound of Formula (I) from the precipitated reaction product comprising the compound of Formula (I), impurities, and/or residual or entrained solvents,

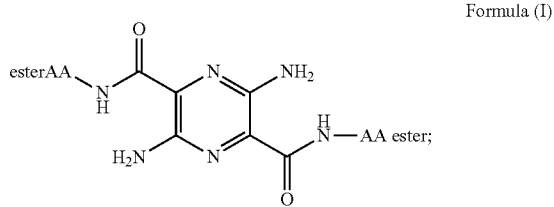

Formula (I)

the methods comprise (a) contacting the precipitated reaction product comprising the compound of Formula (I), impurities, and/or residual or entrained solvents with a solvent forming a first reaction mixture; (b) performing at least one distillation of the first reaction mixture under vacuum maintaining a temperature below 40° C. forming a second reaction mixture; and (c) crystallizing the compound of Formula (I) from the second reaction mixture; wherein the ester portion of the ester amino acid (AA ester) is a $C_1$-$C_{10}$ unsubstituted alkyl or a $C_1$-$C_{10}$ substituted alkyl. The purification, as disclosed herein, does not utilize chromatography and reduces impurities that would carry to the next process steps or steps. Thus, these impurities would not be present or at a low level in the final product. The four-step method may be conducted in a semi-batch or batch process using normal, conventional manufacturing equipment, conventional manufacturing distillation equipment, vacuum, and conventional methods of stirring.

(a) The Compound of Formula (I)

The compound of Formula (I) is described in detail above.

Generally, the amino acid portion of the AA ester or salt thereof of the compound of Formula (I) may be a natural amino acid, an unnatural amino acid, or a synthetic amino acid. In certain embodiments, the amino acid portion of the AA ester or salt thereof of the compound of Formula (I) may be an unnatural amino acid. In specific embodiments, the amino acid portion of the AA ester or salt thereof of the compound of Formula (I) may be serine.

In general, the configuration of the amino acid portion of the AA ester may be a (R) configuration, a (S) configuration, or a racemic mixture. In specific embodiments, the configuration of the amino acid portion may be an (R) configuration, specifically (R)-serine.

Generally, the ester portion of the AA ester of the compound of Formula (I) may be a $C_1$-$C_{10}$ unsubstituted alkyl or a $C_1$-$C_{10}$ substituted alkyl. In various embodiments, the ester portion of the AA ester of the compound of Formula (I) may be a $C_1$-$C_8$ unsubstituted alkyl or a $C_1$-$C_8$ substituted alkyl. In certain embodiments, the ester portion of the AA ester or salt thereof of the compound of Formula (I) may be methyl, ethyl, tert-butyl, or benzyl. In specific embodiments, the ester portion of the AA ester or salt thereof of the compound of Formula (I) is benzyl.

The reaction product from the process comprises the compound of Formula (I), increased impurities, and/or residual or entrained solvents.

a. Step (a)

As discussed above, Step (a) of the four-step process involves contacting the precipitated reaction product comprising the compound of Formula (I), impurities, and/or residual or entrained solvents with a solvent forming a first reaction mixture.

Various solvents can be used in the method. These solvents provide a partial or total solubility of the precipitated reaction product from the process comprising the compound of Formula (I), impurities and/or residual or entrained solvents.

Generally, a wide variety of solvents may be used in the method including protic, aprotic, and mixtures of protic and aprotic solvents. Non-limiting examples of suitable solvents may be selected from a group consisting of toluene, ethyl acetate, propyl acetate, acetone, methyl iso-butyl ketone, 2-butanone, methanol, ethanol, iso-propanol, iso-butanol, water, and mixtures thereof. In certain embodiments, the solvent may be selected from a group consisting of ethyl acetate, propyl acetate, iso-propanol, iso-butanol, water, and mixtures thereof. In specific embodiments, the solvent may be selected from a group consisting of ethyl acetate, isopropanol, water, and mixtures thereof. The water used in step (a) of the four-step method may be deionized water, distilled water, distilled deionized water, or potable (tap) water.

In general, the solvent to the compound of Formula (I) are at a volume (mL) to weight ratio (g) from about 2:1 to about 25:1. In various embodiments, the volume to weight ratio may be about 2:1 to about 25:1, from about 4:1 to about 20:1, or from about 5:1 to about 18.5:1. In one embodiment, the solvent to the compound of Formula (I) are at a volume (mL) to weight ratio (g) from about 15:1 to about 20:1. In another embodiment, the solvent to the compound of Formula (I) are at a volume (mL) to weight ratio (g) from 4:1 to about 6:1.

In general, Step (a) of the four-step method may be conducted at a temperature that ranges from about 10° C. to about 35° C. depending on the solvent or mixtures of solvents utilized. In various embodiments, the temperature of the step (a) may range from about 10° C. to about 35° C., from about 15° C. to about 30° C., or from about 20° C. to about 30° C. In one embodiment, the step (a) of the method may be conducted at temperature of about 23° C. (room temperature). The method is typically performed under ambient pressure. The reaction may also be conducted under an inert atmosphere, for example under nitrogen, argon, helium, and combinations thereof and air.

Generally, Step (a) of the four-step method is allowed to proceed for a sufficient period of time until a slurry is obtained. The duration of the Step (a) of the four-step method may range from about 30 minutes to about 6 hours. In some embodiments, the duration of the method may range from about 30 minutes to about 2 hours, from about 2 hours to about 4 hours, or from about 4 hours to about 6 hours until a slurry is obtained. In one embodiment, the step (a) of the four-step method may be allowed to proceed for about 30 minutes to about 1 hour.

b. Step (b)

Step (b) of the four-step method comprises performing at least one distillation of the first reaction mixture under vacuum maintaining a temperature below 40° C. forming a second reaction mixture. This step removes the entrained, a solvate, or residual solvent in the precipitated reaction product comprising the compound of Formula (I) which was not adequately removed during the precipitation. Step (b) of the four-step method may utilize at least two distillations wherein the second or more distillations may utilize the same solvent or a different solvent as in the first. If a second distillation is utilized, additional solvent may be added to the first reaction mixture before the second distillation. In various embodiments, the solvent is the same solvent or mixture of solvents. In other embodiments, the solvent may be a different solvent or a different mixture of solvents.

Generally, the temperature of Step (b) of the four-step method is conducted to maintain the temperature of the contents of the first reaction mixture under 40° C. In various embodiments, the contents of the first reaction mixture are maintained at a temperature under 40° C., under 30° C., under 20° C., under 10° C., or under 0° C. In one embodiment, the temperature of the contents of the first reaction mixture is maintained under 20° C.

In general, the vacuum used in the distillation in Step (b) of the four-step method is less than 50 inches of Hg. In various embodiments, the vacuum in the distillation of step (b) is less than 50 inches of Hg, less than 40 inches of Hg, less than 30 inches of Hg, or less than 20 inches of Hg. In one embodiment, the vacuum used in the distillation of step (b) of the four-step method is less than 28 inches of Hg.

Generally, the vacuum distillation of Step (b) of the four-step method is conducted until the volume of the first reaction mixture is less than 50% as compared to the initial volume of the first reaction mixture. In various embodiments, the distillation of Step (b) of the four-step method is conducted until the volume is less than 50%, less than 40%, less than 30%, or less than 20% by volume as compared to the initial volume of the first reaction mixture. In one embodiment, the distillation is conducted until the volume of the first reaction mixture is less than 50% as compared to the initial volume of the first reaction mixture. In another embodiment, the distillation is conducted until the volume of the first reaction mixture is less than 25% as compared to the initial volume of the first reaction mixture. If more than one distillation is utilized in Step (b) of the four-step method, the volume of the first reaction mixture after distillation may be the same or different as compared to the initial volume of the first reaction mixture. In another embodiment, the first reaction mixture is distilled in the first distillation to a volume of less than 50% as compared to the initial volume of the first reaction mixture and distilled in the second distillation to a volume less than 25% as compared to the initial volume of the first reaction mixture.

As appreciated by the skilled artisan, the time to conduct Step (b) of the four-step method can and will vary depending on the number of distillations, the size of the batch, the volume of the solvent, the amount of vacuum, and the equipment used.

c. Step (c)

Step (c) of the four-step method cools the second reaction mixture formed after Step (b) and crystallizes the purified compound of Formula (I). The crystals may be of various sizes and shapes. The second reaction mixture may be externally cooled to further reduce the solubility of the compound of Formula (I).

Generally, the second reaction mixture is cooled to a temperature of about 0° C. In various embodiments, the second reaction mixture is cooled to a temperature of about 0° C., less than 0° C., less than −10° C., or lower.

d. Step (d)

Step (d) of the four-step method isolates the purified compound of Formula (I) from the second reaction mixture. The compound comprises purified crystals of the compound of Formula (I).

The purified compound of Formula (I) may be isolated using techniques known in the art such as filtration or centrifugation. After isolating the purified compound of Formula (I), this material is washed and dried until a constant amount of moisture is obtained as measured by a Karl Fisher titration (KF).

In general, the yield of the compound of Formula (I) after conducting the four-step method may be greater than 60%. In various embodiments, the yield may be greater than 60%, greater than 70%, greater than 80%, or greater than 90%. In one embodiment, the yield of the four-step method is greater than 70%.

Generally, the purity of the compound of Formula (I) may be greater than 95% as measured by high-performance liquid chromatography (HPLC), ultra-performance liquid chromatography (UPLC), or other methods known in the art. In various embodiments, the purity of the compound of Formula (I) may be greater than 95%, greater than 97%, greater than 99%, or greater than 99.9%. In one embodiment, the purity of the compound of Formula (I) is greater than 97%.

d. Exemplary Embodiments

In some embodiments, the ester portion of the AA ester or salt thereof of the compound of Formula (I) is (R)-benzyl serine; the solvent is a mixture of ethyl acetate, iso-propanol, and water in Step (a); the solvent to the compound of Formula (I) has a volume (mL) to weight ratio (g) ratio from about 2:1 to about 25:1; the first reaction mixture is distilled under vacuum; the temperature of the distillation is less than 40° C. the vacuum is less than 50 inches of Hg; the volume of the first reaction mixture after distillation is less than 50%; the solvent is isopropanol in Step (b); the solvent to the compound of Formula (I) has a volume (mL) to weight ratio (g) ratio from about 2:1 to about 25:1; the first reaction mixture is distilled under vacuum; the vacuum is less than 50 inches of Hg; the temperature of the distillation is less than 20° C.; the volume of the first reaction mixture after distillation is less than 50% forming a second reaction mixture; the second reaction mixture to a temperature of about 0° C.; and the compound of Formula (I) is isolated from the second reaction mixture. The yield after conducting the four-step process of the compound of Formula (I) is greater than 60% and the purity of the compound of Formula (I) is greater than 95%.

In certain embodiments, the ester portion of the AA ester or salt thereof of the compound of Formula (I) is (R)-benzyl serine; the solvent is a mixture of ethyl acetate, iso-propanol, and water in Step (a); the solvent to the compound of Formula (I) has a volume (mL) to weight ratio (g) ratio from about 15:1 to about 20:1; the first reaction mixture is distilled under vacuum; the temperature of the distillation is less than 40° C., the vacuum is less than 50 inches of Hg; the volume of the first reaction mixture after distillation is less than 50%; the solvent is isopropanol in Step (b); the solvent to the compound of Formula (I) has a volume (mL) to weight ratio (g) ratio from about 4:1 to about 6:1; the first reaction mixture is distilled under vacuum; the temperature of the distillation is less than 20° C.; the vacuum is less than 25 inches of Hg; the volume of the first reaction mixture after distillation is less than 25% forming a second reaction mixture; and the second reaction mixture to a temperature of about 0° C.; and the compound of Formula (I) is isolated from the second reaction mixture. The yield after conducting the four-step process of the compound of Formula (I) is greater than 70% and the purity of the compound of Formula (I) is greater than 97%.

Definitions

When introducing elements of the embodiments described herein, the articles "a", "an", "the" and "said" are intended to mean that there are one or more of the elements. The term "about" is intended to represent ±20%.

In this disclosure, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

As various changes could be made in the above-described methods without departing from the scope of the invention, it is intended that all matter contained in the above description and in the examples given below, shall be interpreted as illustrative and not in a limiting sense.

EXAMPLES

Example 1: Purification of Dibenzyl 2,2'-((3,6-di-aminopyrazine-2,5-dicarbonyl)bis(azanediyl)(2R, 2'R)-bis(3-hydroxypropanoate)

59.02 g of impure dibenzyl 2,2'-((3,6-diaminopyrazine-2,5-dicarbonyl)bis(azanediyl)(2R,2'R)-bis(3-hydroxypropanoate) was reconstituted in EtOAc (500 mL, 8.5 vol) and generated an orange slurry. IPA (295 mL, 5 vol) was added at 20° C. and some solubility was observed. $H_2O$ (295 mL, 5 vol) was added to this mixture and a biphasic and homogenous mixture was obtained. Vacuum distillation was used to remove solvent at $T_j$=20° C./$T_r$=0° C. (28 in Hg) to a volume of 600 mL. As EtOAc was removed an orange slurry was generated and the liquor became a single phase. IPA (295 mL, 5 vol) was charge and vacuum distillation (28 in Hg) was continued at $T_j$=25° C./$T_r$=13° C. until a $V_r$=425 mL (~7.7 vol cf theoretical yield). Vacuum was broken and the orange slurry was cooled to 3° C. and aged for 1 h prior to cold filtration. The reaction vessel was rinsed with IPA/$H_2O$ (1:1 v/v; 120 mL, 2.18 vol), chilled, and was then used to rinse the wet cake. The volume of filtrate obtained from the crystallization of MP-3269 was 219 mL (4 vol). The wet cake was dried in a vacuum oven at 35° C. for 16.5 h to provided 39.04 g MP-3269 (70% yield) as an orange free flowing solid. Analysis by HPLC (25 minute method) indicated a purity of 97.28% AUC and contained 1.17% impurity at RRT=1.03 (m/z=233, positive mode). The material contained 0.59% $H_2O$ by KF analysis.

What is claimed is:
1. A method for purifying a compound of Formula (I) or salt thereof from a precipitated reaction product comprising the compound of Formula (I), impurities, and/or residual or entrained solvents,

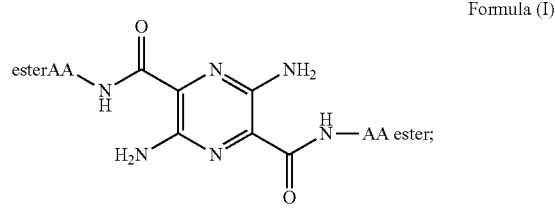

Formula (I)

the method comprising
(a) contacting the precipitated reaction product comprising the compound of Formula (I), impurities, and/or residual or entrained solvents with a first solvent forming a first reaction mixture;
(b) performing at least one distillation of the first reaction mixture under vacuum maintaining a temperature below 40° C. forming a second reaction mixture;

(c) cooling the second reaction mixture to a temperature of about 0° C.; and
(d) isolating the compound of Formula (I) from the second reaction mixture;
wherein "AA ester" is an ester amino acid comprising an ester portion and an amino acid portion, and
wherein the ester portion of the AA ester includes a $C_1$-$C_{10}$ unsubstituted alkyl or a $C_1$-$C_{10}$ substituted alkyl.

2. The method of claim 1, wherein the amino acid portion of the AA ester or salt thereof of the compound of Formula (I) is a natural amino acid, an unnatural amino acid, or a synthetic amino acid.

3. The method of claim 2, wherein the amino acid portion of the AA ester or salt thereof of the compound of Formula (I) has an (R) configuration, a(S) configuration, or a mixture thereof.

4. The method of claim 2, wherein the amino acid portion of the AA ester or salt thereof of the compound of Formula (I) is (R)-serine.

5. The method of claim 2, wherein the ester portion of the AA ester or salt thereof of the compound of Formula (I) is methyl, ethyl, tert-butyl, or benzyl.

6. The method of claim 2, wherein the ester portion of the AA ester or salt thereof of the compound of Formula (I) is benzyl.

7. The method of claim 1, wherein the ester portion of the AA ester or salt thereof of the compound of Formula (I) is a $C_1$-$C_8$ unsubstituted alkyl or a $C_1$-$C_8$ substituted alkyl.

8. The method of claim 1, wherein the at least one distillation in step (b) comprises at least two distillations.

9. The method of claim 8, wherein a second solvent is added between distillations.

10. The method of claim 9, wherein the second solvent may be the same as or different from the first solvent used in step (a).

11. The method of claim 1, wherein the first reaction mixture is distilled to a volume of less than 50% as compared to the initial volume of the first reaction mixture.

12. The method of claim 11, wherein the first reaction mixture is distilled to a volume less than 25% as compared to the initial volume of the first reaction mixture.

13. The method of claim 1, wherein the first solvent is selected from the group consisting of toluene, ethyl acetate, propyl acetate, acetone, methyl iso-butyl ketone, 2-butanone, methanol, ethanol, iso-propanol, iso-butanol, water, and mixtures thereof.

14. The method of claim 13, wherein the first solvent is selected from the group consisting of ethyl acetate, isopropanol, water, and mixtures thereof.

15. The method of claim 1, wherein the first solvent and the compound of Formula (I) are present at a volume (mL) to weight ratio (g) from about 2:1 to about 25:1.

16. The method of claim 15 wherein the first solvent and the compound of Formula (I) are present at a volume (mL) to weight ratio (g) from about 15:1 to about 20:1.

17. The method of claim 15, wherein the first solvent and the compound of Formula (I) are present at a volume (mL) to weight ratio (g) from 4:1 to about 6:1.

18. The method of claim 1, wherein the temperature is maintained in step (b) at less than 20° C.

19. The method of claim 1, wherein the vacuum is less than 50 inches of Hg.

20. The method of claim 19, wherein the vacuum is less than 28 inches of Hg.

21. The method of claim 1, wherein the compound of Formula (I) has a yield greater than 60%.

22. The method of claim 1, wherein the compound of Formula (I) has a yield greater than 70%.

23. The method of claim 1, wherein the compound of Formula (I) has a purity greater than 95%.

24. The method of claim 1, wherein the compound of Formula (I) has a purity greater than 97%.

25. A method for purifying a compound of Formula (I) or salt thereof from a precipitated reaction product comprising the compound of Formula (I), impurities, and/or residual or entrained solvents,

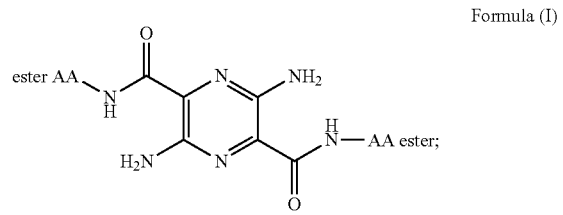

Formula (I)

the method comprising:
(a) contacting the precipitated reaction product comprising the compound of Formula (I), impurities, and/or residual or entrained solvents with a first solvent comprising a mixture of ethyl acetate, isopropanol, and water, thereby forming a first reaction mixture wherein the first solvent and the compound of Formula (I) are present at a volume (mL) to weight (g) ratio from about 2:1 to about 25:1;
(b1) performing a first distillation of the first reaction mixture under vacuum maintaining a temperature below 40° C. forming a second reaction mixture, wherein the vacuum is less than 50 inches of Hg and the volume of the first reaction mixture after distillation is less than 50% as compared to the initial volume of the first reaction mixture;
(b2) adding a second solvent to the distilled first reaction mixture to form a second reaction mixture, the second solvent comprising isopropanol, wherein the second solvent and the compound of Formula (I) are present at a volume (mL) to weight (g) ratio from about 2:1 to about 25:1;
(b3) performing a second distillation of the second reaction mixture under vacuum maintaining a temperature below 20° C. forming a third reaction mixture, wherein the vacuum is less than 50 inches of Hg and the volume of the first reaction mixture after distillation is less than 50% as compared to the initial volume of the first reaction mixture;
(c) cooling the third reaction mixture to a temperature of about 0° C.; and
(d) isolating the compound of Formula (I) from the third reaction mixture;
wherein "AA ester" is an ester amino acid comprising an ester portion and an amino acid portion, and
wherein the AA ester is

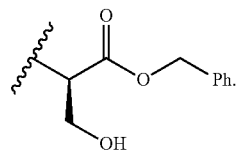 [SMILES: *[C@H](CO)C(=O)OCc1ccccc1]

26. The method of claim 25, wherein the compound of Formula (I) has a yield greater than 60%.

27. The method of claim 25, wherein the compound of Formula (I) has a purity greater than 95%.

28. A method for purifying a compound of Formula (I) or salt thereof from a precipitated reaction product comprising the compound of Formula (I), impurities, and/or residual or entrained solvents,

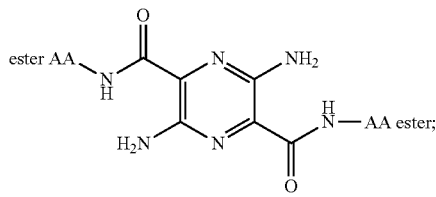

Formula (I)

the method comprising:
(a) contacting the precipitated reaction product comprising the compound of Formula (I), impurities, and/or residual or entrained solvents with a first solvent comprising a mixture of ethyl acetate, isopropanol, and water, thereby forming a first reaction mixture wherein the first solvent and the compound of Formula (I) are present at a volume (mL) to weight (g) ratio from about 15:1 to about 20:1;
(b1) performing a first distillation of the first reaction mixture under vacuum maintaining a temperature below 40° C. forming a second reaction mixture, wherein the vacuum is less than 50 inches of Hg and the volume of the first reaction mixture after distillation is less than 50% as compared to the initial volume of the first reaction mixture;
(b2) adding a second solvent to the distilled first reaction mixture to form a second reaction mixture, the second solvent comprising isopropanol, wherein the second solvent and the compound of Formula (I) are present at a volume (mL) to weight (g) ratio from about 4:1 to about 6:1;
(b3) performing a second distillation of the second reaction mixture under vacuum maintaining a temperature below 20° C. forming a third reaction mixture, wherein the vacuum is less than 25 inches of Hg and the volume of the first reaction mixture after distillation is less than 25% as compared to the initial volume of the first reaction mixture;
(c) cooling the third reaction mixture to a temperature of about 0° C.; and
(d) isolating the compound of Formula (I) from the third reaction mixture;
wherein "AA ester" is an ester amino acid comprising an ester portion and an amino acid portion, and
wherein the amino acid portion of the AA ester is (R)-serine.

29. The method of claim 28, wherein the compound of Formula (I) has a yield greater than 70%.

30. The method of claim 28, wherein the compound of Formula (I) has a purity greater than 97%.

* * * * *